(12) United States Patent
Yoo (10) Patent No.: US 9,861,591 B2
(45) Date of Patent: Jan. 9, 2018

(54) NITRIC OXIDE-RELEASING WOUND TREATMENT FILM AND PREPARATION METHOD THEREFOR

(71) Applicant: Pusan National University Industry-University Cooperation Foundation, Busan (KR)

(72) Inventor: Jin Wook Yoo, Busan (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 15/122,182

(22) PCT Filed: Feb. 26, 2015

(86) PCT No.: PCT/KR2015/001864
§ 371 (c)(1),
(2) Date: Aug. 29, 2016

(87) PCT Pub. No.: WO2015/130096
PCT Pub. Date: Sep. 3, 2015

(65) Prior Publication Data
US 2016/0367492 A1    Dec. 22, 2016

(30) Foreign Application Priority Data

Feb. 28, 2014  (KR) .................. 10-2014-0024051
Feb. 25, 2015  (KR) .................. 10-2015-0026410

(51) Int. Cl.
*A61K 47/36*    (2006.01)
*A61K 33/26*    (2006.01)
(Continued)

(52) U.S. Cl.
CPC .......... *A61K 9/7007* (2013.01); *A61K 9/0014* (2013.01); *A61K 33/00* (2013.01);
(Continued)

(58) Field of Classification Search
CPC ................................ A61K 47/36; A61K 33/26
See application file for complete search history.

(56) References Cited

U.S. PATENT DOCUMENTS 6,391,895 B1 * 5/2002 Towart ................. C07D 213/65
                                                514/184
8,404,266 B2 * 3/2013 Lacza .................. A61K 9/0014
                                                424/425
(Continued)

FOREIGN PATENT DOCUMENTS

| KR | 10-2002-0066024 A | 8/2002 |
| KR | 10-2008-0037677 A | 4/2008 |
| WO | 2007-149520 A2 | 12/2007 |

OTHER PUBLICATIONS

Domjan et al (Macromolecules, 2009, 42, 4667-4673).*
(Continued)

*Primary Examiner* — Benjamin Packard
(74) *Attorney, Agent, or Firm* — Revolution IP, PLLC (57) ABSTRACT

Provided is a nitric oxide-releasing wound treatment film containing S-nitroglutathione, which is a nitric oxide donor to be spontaneously formed in the human body, has mechanical characteristics enabled to be applied to the human body, slowly releases nitric oxide and inhibits a pathogen, which is the main cause of wound infection, and can quickly heal a wound, and thus the film can be useful for treating a wound.

6 Claims, 8 Drawing Sheets

(51) Int. Cl.
    *A61K 9/70*     (2006.01)
    *A61K 38/06*     (2006.01)
    *A61K 9/00*     (2006.01)
    *A61K 33/00*     (2006.01)
    *A61K 47/10*     (2017.01)
    *A61L 15/44*     (2006.01)

(52) U.S. Cl.
    CPC ............ *A61K 33/26* (2013.01); *A61K 38/063* (2013.01); *A61K 47/10* (2013.01); *A61K 47/36* (2013.01); *A61L 15/44* (2013.01); *A61L 2300/114* (2013.01)

(56) References Cited

U.S. PATENT DOCUMENTS

2008/0069848 A1     3/2008     Peters
2013/0084336 A1     4/2013     Friedman et al.

OTHER PUBLICATIONS

International Search Report for PCT/KR2015/001864 dated May 27, 2015 from Korean Intellectual Property Office.
Seabra, A. B. et al., "Solid Films of Blended Poly(Vinyl Alcohol)/Poly (Vinyl Pyrrolidone) for Topical S-itrosoglutathione and Nitric Oxide Release", Journal of pharmaceutical sciences, 2005, vol. 94, No. 5, pp. 994-1003.
Seabra, A. B. et al., "Poly(vinyl alcohol) and poly(vinyl pyrrolidone) blended films for local nitric oxide release", Biomaterials, 2004, vol. 25, No. 17, pp. 3773-3782.

\* cited by examiner

NITRIC OXIDE-RELEASING WOUND TREATMENT FILM AND PREPARATION METHOD THEREFOR

CROSS REFERENCE TO PRIOR APPLICATIONS

This application is a National Stage Application of PCT International Patent Application No. PCT/KR2015/001864 filed on Feb. 26, 2015, under 35 U.S.C. §371, which claims priority to Korean Patent Application Nos. 10-2014-0024051 filed on Feb. 28, 2014 and 10-2015-0026410 filed on Feb. 25, 2015 which are all hereby incorporated by reference in their entirety.

TECHNICAL FIELD

The present invention relates to a nitric oxide-releasing wound treatment film and a method of preparing the same, which inhibits a pathogen of main cause of wound infection and can quickly treat a wound.

BACKGROUND ART

Skin covering the outside of our body is exposed to various dangerous and physical damages from daily life. Accordingly, a number of factors surrounding us cause injuries such as the skin wound by mechanical damage, bruises, burns, etc. A wound refers to a state where the anatomical continuity of human tissue has lost its original continuity by an external action. Our skin consists of dermis, epidermis and subcutaneous fat, for example these dermis or epidermis and subcutaneous fat, etc., lose their continuity by external injury such as being cut or fallen and get wounded.

In general, wound dressing is used to treat effectively a skin wound such as a wound or a trauma. The requirements of the wound dressing are the holding ability of proper humidity in the contact surface with the wound; the control ability of the wound secretion; easy attachment and removal of the wound dressing; permeability of air and water vapor between the wound and the surroundings; external thermal insulation of the wound; resistance to invasion of bacteria; non-toxicity in human body; and good mechanical properties.

An ointment is the most popular wound healing method and it includes Madecassol (Dongkuk Pharmaceutical), CENTICA® -S (Samjin Pharm Co., Ltd,) and Tinadex (Chong Kun Dang Pharm.).

A prior art of the present invention is disclosed in Korea Patent Publication No. 2002-0066024.

DISCLOSURE

Technical Problem

An object of the present invention is to provide a nitric oxide-releasing wound treatment film containing S-nitrosoglutathione, which is a nitric oxide donor to be spontaneously formed in the human body and a preparation method therefor.

Technical Solution

To achieve the object of the present invention, an aspect of the present invention provides a nitric oxide-releasing wound treatment film comprising a nitric oxide donor encapsulated in a polymer.

Also, the nitric oxide donor may be selected from the group consisting of S-nitrosoglutathione, diazeniumdiolate, an organic nitrate and iron-nitrosyl complexes.

In addition, the polymer may be a biocompatible polymer selected from the group consisting of chitosan, silicone, polyurethane and calcium alginate.

In addition, the nitric oxide donor of 2.5 to 30 weight % may be comprised in respect of the film of 100 weight %.

According to another aspect of the present invention provides a method of preparing a nitric oxide-releasing wound treatment film, comprising: preparing a polymer solution by solubilizing a polymer in a solvent, adjusting pH and adding a plasticizer; preparing a reaction mixture by adding and mixing a nitric oxide donor into the polymer solution; and casting the reaction mixture in form of film and drying it in a dehumidified darkroom.

Also, the nitric oxide donor may be selected from the group consisting of S-nitrosoglutathione, diazeniumdiolate, an organic nitrate and iron-nitrosyl complexes.

In addition, the polymer may be selected from the group consisting of chitosan, silicone, polyurethane and calcium alginate.

In addition, the plasticizer may be selected from the group consisting of polyethyleneglycol, sorbitol and glycerol.

Also, the polymer solution may be prepared by adjusting pH 4.0 to pH 6.0 using 0.1M acetic acid buffer solution.

The nitric oxide donor of 2.5 to 30 parts by weight may be added into the polymer solution of 100 parts by weight.

The drying may be performed at a temperature of 25 to 37° C. for 1 to 2 days.

Advantageous Effects

According to the present invention, a nitric oxide-releasing wound treatment film containing S-nitrosoglutathione, which is a nitric oxide donor to be spontaneously formed in the human body, has mechanical characteristics enabled to be applied to the human body, slowly releases nitric oxide and inhibits a pathogen, which is the main cause of wound infection, and can quickly heal a wound, and thus the film can be useful for treating a wound.

BEST MODE

NO releasing films were prepared by the solvent evaporation method. Chitosan was dissolved in acetone buffer (100 mM) and pH of the solution was adjusted using an acetic acid to 4.4. Glycerol was added to the chitosan solution to reach a final concentration of 1% (w/w). GSNO of 10 mg was added to the solution and stirred for 20 minutes. The resulting solution was casted in the petri dish, and, was dried using a dryer equipped with a dehumidifier at 37° C. for 2 days in the darkroom. The prepared film (hereinafter referred to as "CS/NO film") was stored at 7° C. and under vacuum. At this time, a blank film which does not contain GSNO was prepared as a control group.

In particular, drying of the film was performed in darkroom under dehumidifying condition to promote evaporation and the reddish transparent and uniform film having a loading efficiency of 47% nitric oxide donors can be obtained, while drying in dry oven without dehumidification condition exhibited the loading efficiency of 20% or less Meanwhile, to compare in vivo wound healing effects, another polymer except for chitosan as a carrier, polyvinyl alcohol (poly vinyl alcohol; PVA, Sigma Adlrich, MO, USA) was used and PVA solution of 1% (w/w) was prepared by applying heat and a film was prepared in the same manner as CS/NO film (hereinafter referred to as "PVA/NO film").

Hereinafter, the present invention is explained in more detail.

The inventors of the present invention confirmed a nitric oxide-releasing wound treatment film containing S-nitrosoglutathione, which is a nitric oxide donor to be spontaneously formed in the human body, has mechanical characteristics enabled to be applied to the human body, slowly releases nitric oxide and inhibits a pathogen, which is the main cause of wound infection, and can quickly heal a wound, and thus the film can be useful for treating a wound and completed the present invention.

Therefore, the present invention provides a nitric oxide-releasing wound treatment film comprising a nitric oxide donor encapsulated in a polymer.

The nitric oxide donor may be selected from the group consisting of S-nitrosoglutathione, diazeniumdiolate, an organic nitrate and iron-nitrosyl complexes and in particular, it is preferably to be S-nitrosoglutathione, because it is spontaneously formed in the human body to be harmless and has excellent stability during manufacture and storage process.

The polymer may be a biocompatible polymer selected from the group consisting of chitosan, silicone, polyurethane and calcium alginate and it is preferably to be chitosan, because it has wound healing by itself with absorbing wound secretion and maintaining moisture around the wound surface The nitric oxide donor of 2.5 to 30 weight % may be comprised in respect of the film of 100 weight %. A nitric oxide donor is a material which releases nitric oxides (hereinafter referred to as 'NO') after mixing with polymer solution and drying. If the nitric oxide donor less than 2.5 weight % is added, NO releasing amount is low and the wound healing effect is decreased not to be continuously released, and if the nitric oxide donor larger than 30 weight % is added, the overall production efficiency of the wound treatment film is reduced and also, mechanical properties and stability is reduced.

In addition, the present invention provides a method of NO-releasing wound treatment film by a solvent evaporation method. More specifically, the method comprises: preparing a polymer solution by solubilizing a polymer in a solvent, adjusting pH and adding a plasticizer; preparing a reaction mixture by adding and mixing a nitric oxide donor into the polymer solution; and casting the reaction mixture in form of film and drying it in a dehumidified darkroom.

According to an embodiment of the present invention, the method comprises: preparing a polymer solution by solubilizing a polymer such as chitosan in a solvent, adjusting pH by an acidifier and adding glycerol; preparing a reaction mixture by adding and stirring a nitric oxide donor such as S-nitrosoglutathione (hereinafter referred to as 'GSNO') into the polymer solution; and casting the reaction mixture in form of film and drying it in a dehumidified darkroom.

The polymer solution may be prepared by adjusting pH 4.0 to pH 6.0 using 0.1M acetic acid buffer solution.

If the pH of the polymer solution is adjusted by weak acid and nitric oxide donor is mixed, GSNO can be mixed homogeneously in the polymer solution and it does not affect the stability of GSNO.

The plasticizer may be selected from the group consisting of polyethyleneglycol, sorbitol and glycerol, and among them, glycerol can increase the mechanical properties by increasing the availability of the wound treatment film.

The nitric oxide donor of 2.5 to 30 parts by weight may be added into the polymer solution of 100 parts by weight and the stirring may be performed for 10 to 60 minutes, preferably for 20 minutes. If the amount of the nitric oxide donor exceeds the range, the phase separation is occurred to cause an appearance problem and decrease in mechanical properties.

The drying may be performed at a temperature of 25 to 37° C. for 1 to 2 days. If the drying temperature falls beyond the above range, problems of film transparency and the stability of GSNO can be caused.

In particular, drying the cast film a dark room under dehumidified conditions shows the loading efficiency of nitric oxide donor of 47%, and on the other hand, drying without dehumidified conditions causes a problem of the loading efficiency of the nitric oxide donor of at most 20%

The present invention will be described more fully hereinafter with reference to the accompanying drawings, in which exemplary embodiments of the invention are shown.

EXAMPLE 1

Synthesis of Gsno

GSNO was synthesized as described previously (Tetrahedron Lett, 1985; 26: 2013-2016). Briefly, reduced L-glutathione (Sigma Adlrich, MO, USA) of 1.005 g was dissolved in 2M HCl (Daejung) at 4° C. to produce a solution with the final concentration of 0.625 mM. Sodium nitrite (sigma Adlrich, MO, USA) of 220.6 mg was added to the solution and the mixture was placed in an ice bath under stirring for 30 min. The final solution was precipitated with 80% cold acetone and stirred for another 20 min. The stirred solution was centrifuged at 4° C. and 20,000 g for 20 min. A cold 100% acetone of 20 mL was added to the precipitate and centrifuged. 100% diethylether of 20 mL was added to the obtained precipitate and centrifuged. The pink powder GSNO was further freeze-dried for 24 hours and kept at -20° C. until further use.

EXAMPLE 2

Preparation of No Releasing Film

An NO releasing film was prepared by a solvent evaporation method. Briefly, chitosan was dissolved in acetone buffer (100 mM) and pH of the solution was adjusted using an acetic acid to 4.4. Glycerol was added to the chitosan solution to reach a final concentration of 1% (w/w). GSNO of 10 mg was added to the solution and stirred for 20 minutes. The resulting solution was casted in the petri dish, and, was dried using a dryer equipped with a dehumidifier at 37° C. for 2 days in the darkroom. The prepared film (hereinafter referred to as "CS/NO film") was stored at 7° C. and under vacuum. At this time, a blank film which does not contain GSNO was prepared as a control group.

In particular, drying of the film was performed in darkroom under dehumidifying condition to promote evaporation and the reddish transparent and uniform film having a loading efficiency of 47% nitric oxide donors can be obtained, while drying in dry oven without dehumidification condition exhibited the loading efficiency of 20% or less Meanwhile, to compare in vivo wound healing effects, another polymer except for chitosan as a carrier, polyvinyl alcohol (poly vinyl alcohol; PVA, Sigma Adlrich, MO, USA) was used and PVA solution of 1% (w/w) was prepared by applying heat and a film was prepared in the same manner as CS/NO film (hereinafter referred to as "PVA/NO film").

EXAMPLE 3

Characterization of No-releasing Film

1. Film Thickness

The thickness of the films prepared in the Example 2 was measured using a digital outside micrometer (Bluebird Multinational Co.) at five different locations (center and four corners). The mean of the thickness measurements was considered as the film thickness.

As a result, the mean thickness of the blank film and NO releasing film at center and four corners are 61.2±4.5 μm and 64.6±8.6 μm, respectively, which showing that the thickness of the film was not changed by the addition of GSNO.

2. Scanning Electron Microscope (SEM) Analysis

The surface morphology of the films prepared in the Example 2 was examined using a field emission scanning electron microscope (FE-SEM, S4800, Hitachi, Japan). Samples (1.5×1.5 cm$^2$) were mounted on a double-sided carbon tape and coated with platinum for 2 min under vacuum. The samples were viewed under the FE-SEM at an acceleration voltage of 1-5 kV.

Figure 1:
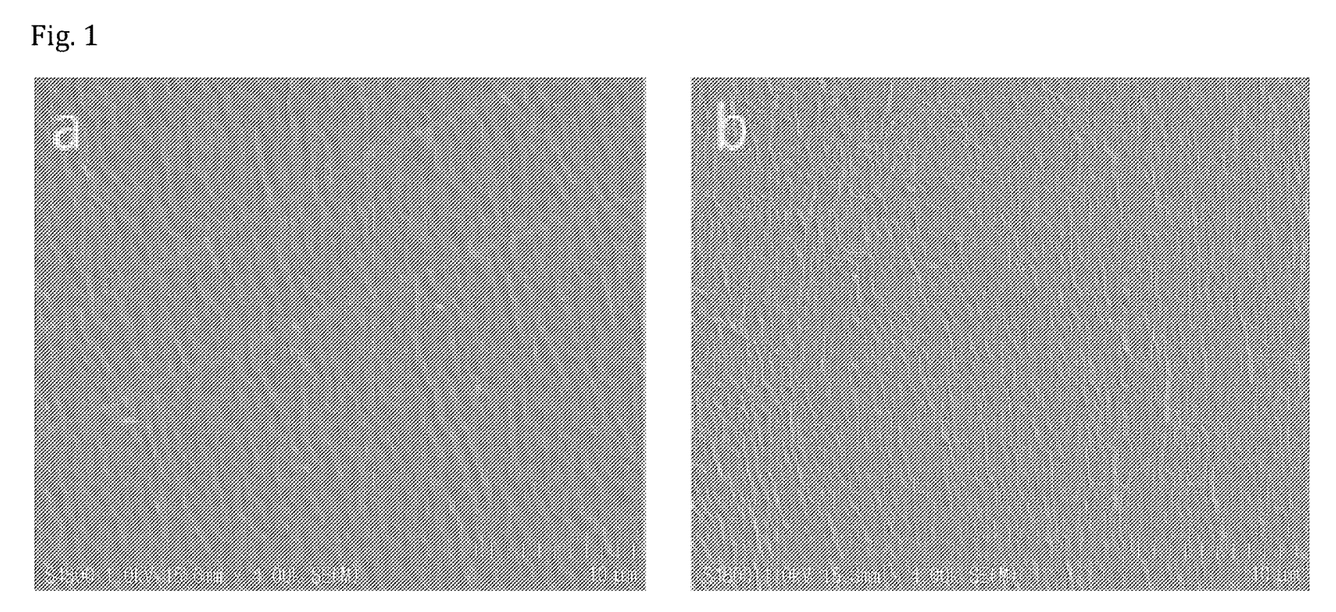
FIG. 1 illustrates a surface morphology of the (a) chitosan film and (b) GSNO film determined by SEM analysis.

As shown in FIG. 1, a blank film had a homogenous, smooth surface morphology, and the incorporation of GSNO did not alter the surface morphology of the film.

3. Thermal Properties

The thermal properties of bare GSNO, blank film and CS/NO film were examined using a differential scanning calorimeter (DSC, N-650, SCINCO, Korea). Each sample was heated in a completely sealed aluminum pan at a rate of 5° C./min from 30° C. to 200° C. in a dynamic nitrogen atmosphere.

Figure 2:
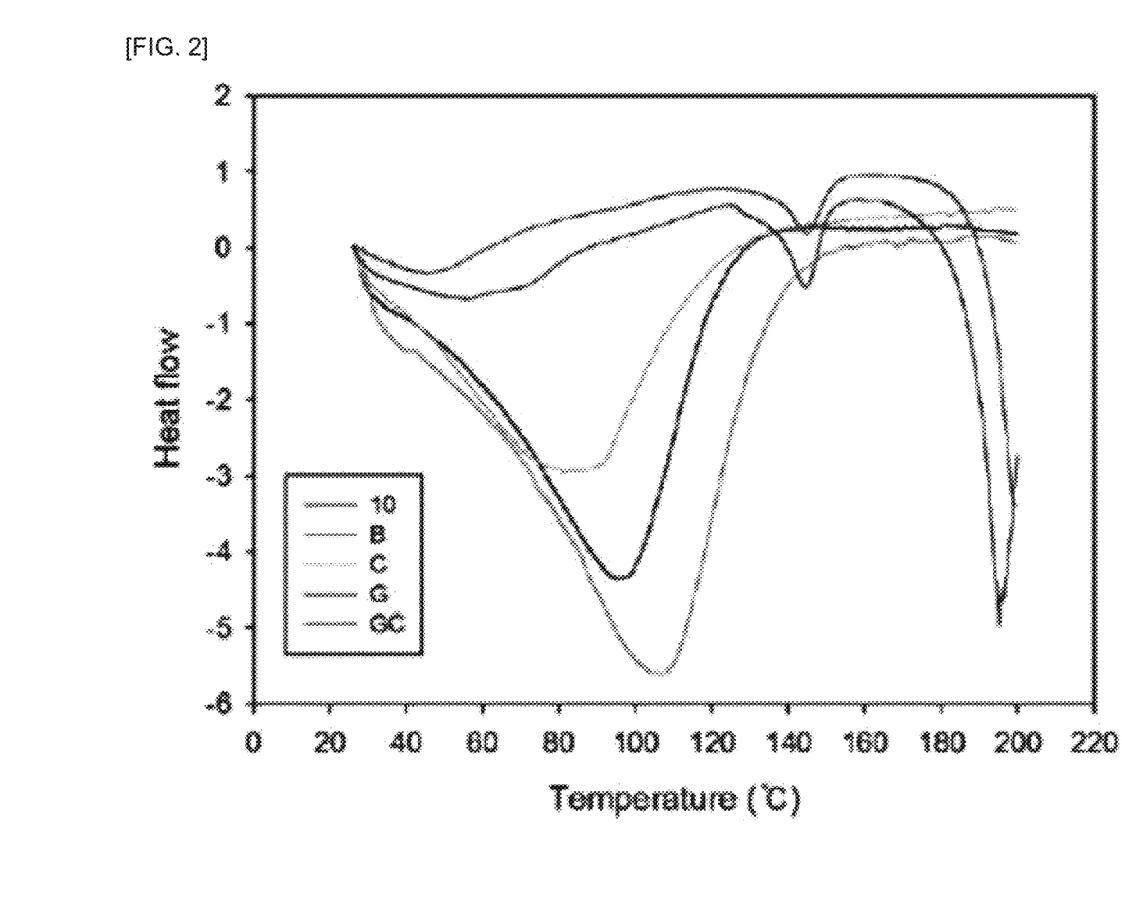
FIG. 2 is a thermal properties of the GSNO film (10), chitosan film (B), chitosan (C), GSNO (G) and mixture of GSNO and chitosan (GC).

As shown in FIG. 2, GSNO exhibited a strong endothermic peak at 195° C. and chitosan exhibited a weaker endothermic peak compared to that of GSNO. However, the peak for the melting point of GSNO disappeared in CS/NO film, indicating that GSNO fully dissolved and molecularly dispersed in the film. A broad endothermic peak was observed below 140° C. for both films; this could be attributed to the evaporation of absorbed moisture from the films.

4. Mechanical Properties

To investigate the mechanical properties of the CS/NO film prepared in the Example 2, tensile strength (TS) and percentage elongation at break were measured using a tensile test machine (Instron 3345, Norwood, Mass., USA). Firstly, the films were cut into a specific dog bone shape (80 mm in length and 30 mm in width). The tests were performed at a stretching rate of 10 mm/min and the thickness of the film was measured with a caliper just before the examinations. Percentage elongation at break (E%) was calculated from the difference between the initial length of the sample (30 mm) and the extended length at the moment of breakage.

As shown in Table 1, the elongation at break was not affected by the addition of NO. A blank film has been stretched to 134.4±11.5% compared to the initial length; NO releasing fila was around 129,9±18.1%. However, addition of GSNO reduced the tensile strength and Young's modulus.

TABLE 1

|  | Tensile strength (MPa) | Elongation at break (%) | Young's modulus(MPa) |
| --- | --- | --- | --- |
| Blank | 7.87 ± 1.02 | 134.4 ± 11.5 | 7.18 ± 0.53 |
| NO 10 mg | 6.53 ± 0.70 | 129.9 ± 18.1 | 5.48 ± 0.31 |

5. NO Release Study

CS/NO films were cut into a square equivalent to 50 mg and immersed in 10 mL of phosphate-buffered saline (PBS, pH 7.4) at 37° C. NO released from the film was analyzed using Griess reagent. At predetermined time intervals, 100 μl of PBS was removed and replaced with fresh PBS. After an appropriate dilution, Griess reagent was added at a ratio of 1:1. The obtained mixtures of 100 μl were added to the wells of 96-well plates and placed for 30 min at room temperature in the dark. Finally, the amount of nitrite was measured using a micro plate reader at a wavelength of 540 nm.

Figure 3:
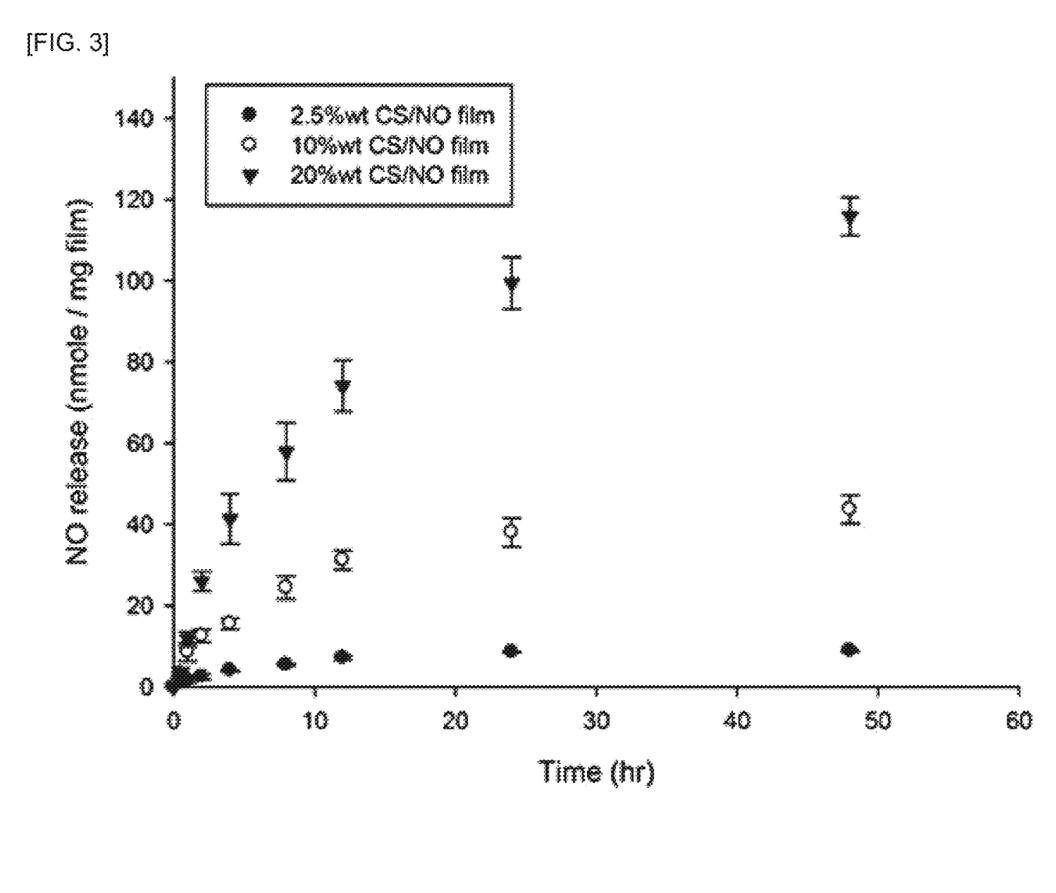
FIG. 3 is NO release profiles of GSNO films.

As shown in FIG. 3, NO release profiles from the NO releasing films exhibited first order exponential function. In the initial one hour, the release of NO from the film was slow and then was done according to the linear equation. The initial slow release can be attributed to the time required for hydration of the film. Since the CS/NO films need to swell for the release of NO, the lag time during the initial hours of NO release was expected. Among the films loaded with different doses of GSNO, the CS/NO film containing 20 wt % GSNO released the highest amount of NO in a sustained manner for over 48 hours, presuming that the CS/NO film is able to release the most sufficient amount of NO during the duration of wound treatment.

6. Anti-bacterial Activity Assay

Figure 4:
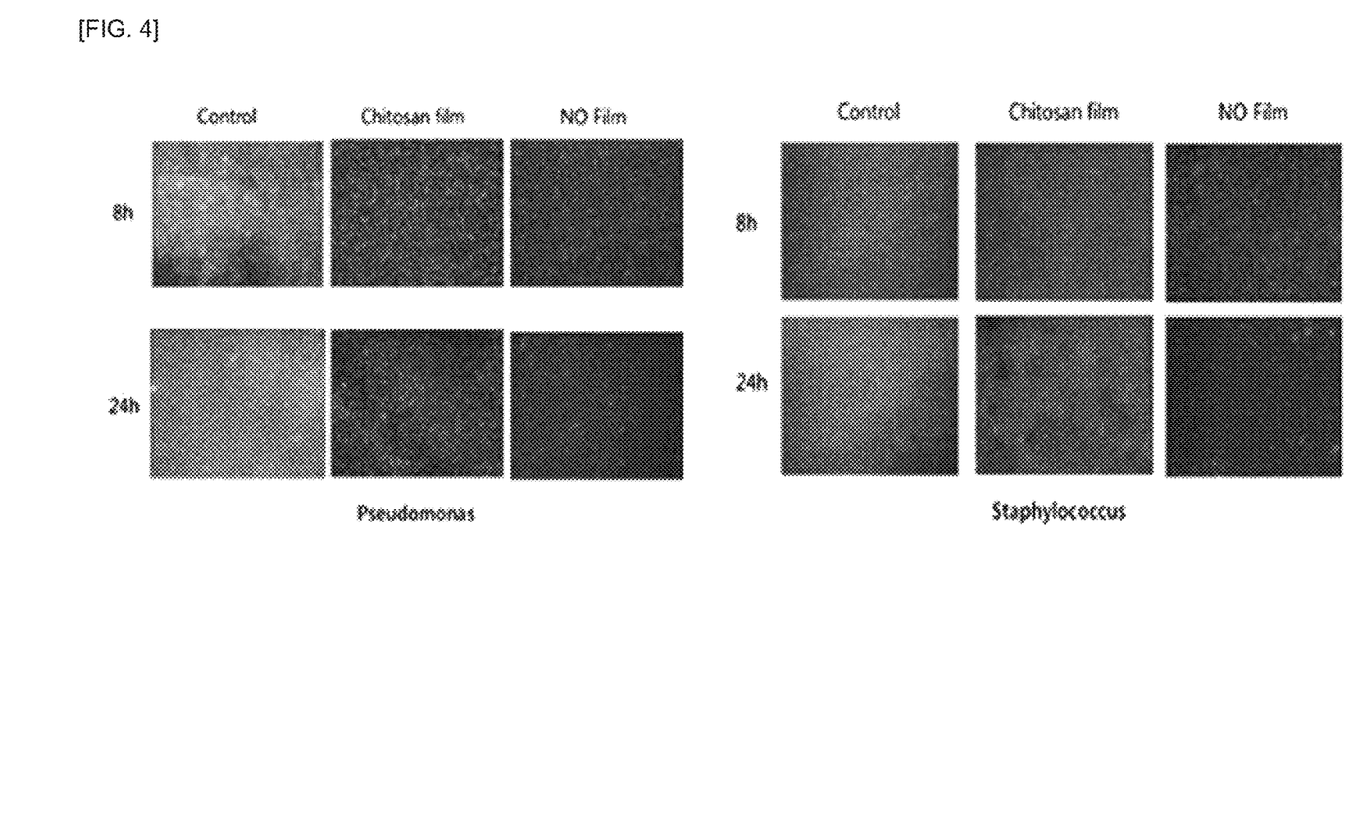
FIG. 4 is antibacterial activities and antibacterial efficacy against gram-positive bacillus and gram-negative bacillus of the NO releasing film.

FIG. 4 is antibacterial activities and antibacterial efficacy against gram-positive bacillus and gram-negative bacillus of the NO releasing film.

The strains of bacteria used for this study were *P aeruginosa* PAO1 (wild-type prototroph, Peerson et al., 1997), *S. aureus* RN4220 (Kreiswirth et al., 1983) or Methicillin-resistant *Staphylococcus*. *S. aureus* were cultured in LB broth of 3 mL with vigorous shaking and grown overnight. Then, cells were inoculated on a cover glass of 12-well plates and incubated in a LB broth media of 2 mL containing antibiotics of 2 μl. Then, a piece of the blank film and the CS/NO film (1.3×1.3 cm$^2$) was placed on a well of the glass cover slip. At intervals of the predetermined time, the glass cover slips were gently washed with sterile water to remove the non-adherent *S. aureus* bacteria. The bacteria on the glass cover slips were observed under a fluorescence microscopy. For *P. aeruginosa*, aliquot of minimal medium of 2 mL containing antibiotics of 25 μl and a plasmid inducer was inoculated on glass cover slip of 12-well plates. *P. aerugi-* nosa of 40 μl, was inoculated on a glass cover slip of each well plate and the film was added the well plates. At intervals of the predetermined time, the glass cover slips were gently washed with sterile water to remove the non-adherent *P. aeruginosa* bacteria. The bacteria on the glass cover slips were observed under a fluorescence microscopy.

The reduction in viability of *P aeruginosa* was observed with the CS/NO film than CS film in 8 hours and after 24 hours, the more prominent reduction was observed.

After 24 hours, the significantly more prominent reduction in viability of *S. aureus* was observed with the CS/NO film than CS film.

7. In Vivo Wound-healing Assay

To evaluate the in vivo wound-healing efficacy of the CS/NO film, male Sprague-Dawley rats weighing 250-280 g were chosen as an animal model. Prior to the development of wounds on the dorsal area, the rats were anesthetized using Zoletil 50® (tiletamine/zolazepam) and Rompun® (xylazine hydrochloride) at a ratio of 5:2. Dorsal hair was removed with an electric razor. Subsequently, back skin was excised to create full-thickness wounds (1.5 cm×1.5 cm). A *P. aeruginosa* solution (3.2×1088888 cells/mL) of 50 μl was dropped to each wound and incubated to make the infectious wounds.

Each wound was covered with Mediform® (Mundipharma, control), PVA/NO film prepared in the Example 2 or CS/NO film. All materials were covered and fixed with an elastic adhesive tape (Micropore, 3M Consumer Health Care, St Paul, Minn., USA). Every dressing on wound lesions was replaced with a new dressing at proper times.

All rodents were cared for in separate cages, and digital images of the lesions were collected every 3 days by using a digital camera. The macroscopic changes in the wounds were detected by digital image for a period of 4, 7, 10, 13 and 16 days after occurrence of the wound. The wound size reduction and epithelialization rates were determined and calculated as follows.

Epithelialization rate (%)=$E_t/(W_t+W_0)\times 100$ where $E_t$ is the epithelialized area at time t, $W_t$ is the wound area at time t and $W_0$ is the wound area at initial time.

Figure 5:
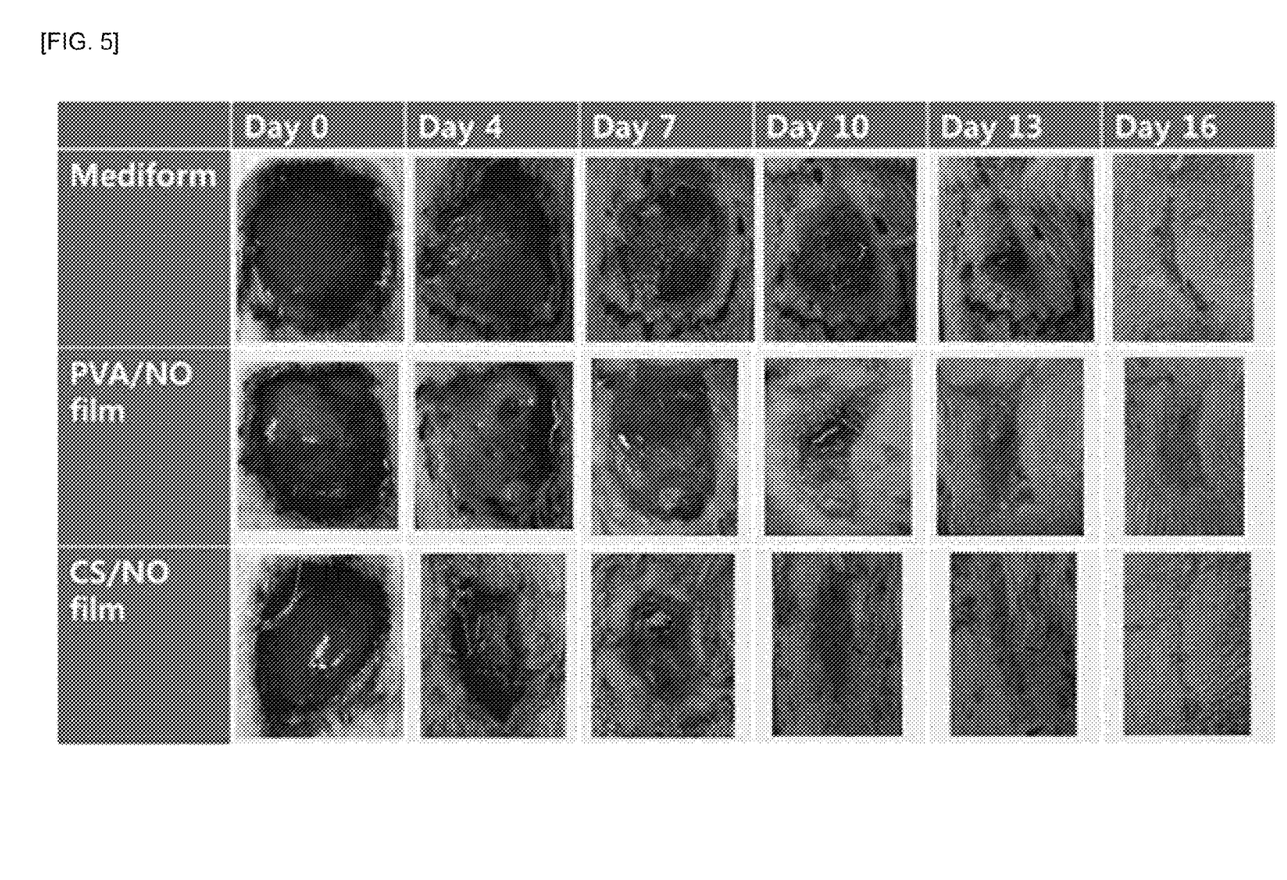
FIG. 5 is representative photographs of wounds treated with NO releasing film according to treatment period.

FIG. 5 is macroscopic appearances of the wounds according to temporary changes after the operation and severe inflammation in the wound area was observed in each group of rats on postoperative day (POD) 3, while those treated with CS/NO films showed faster closure.

Figure 6:
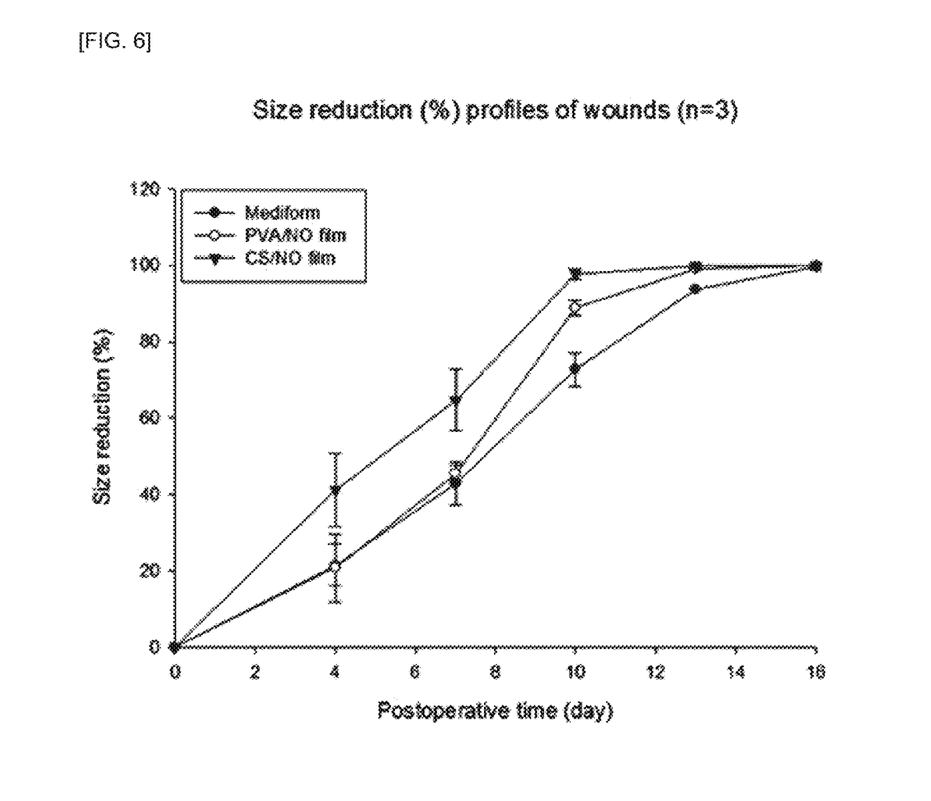
FIG. 6 is size reduction profiles of wounds treated with NO releasing film.

FIG. 6 shows size reduction profiles of wounds treated with NO releasing film. At POD 10, the wounds in the rats treated with the CS/NO film, were almost closed with significant differences in wound sizes compared to those in the control. In addition, the wounds in the rats treated with the PVA/NO film also exhibited the beneficial effects in wound-healing process, which is slower than those treated with the CS/NO film.

Figure 7:
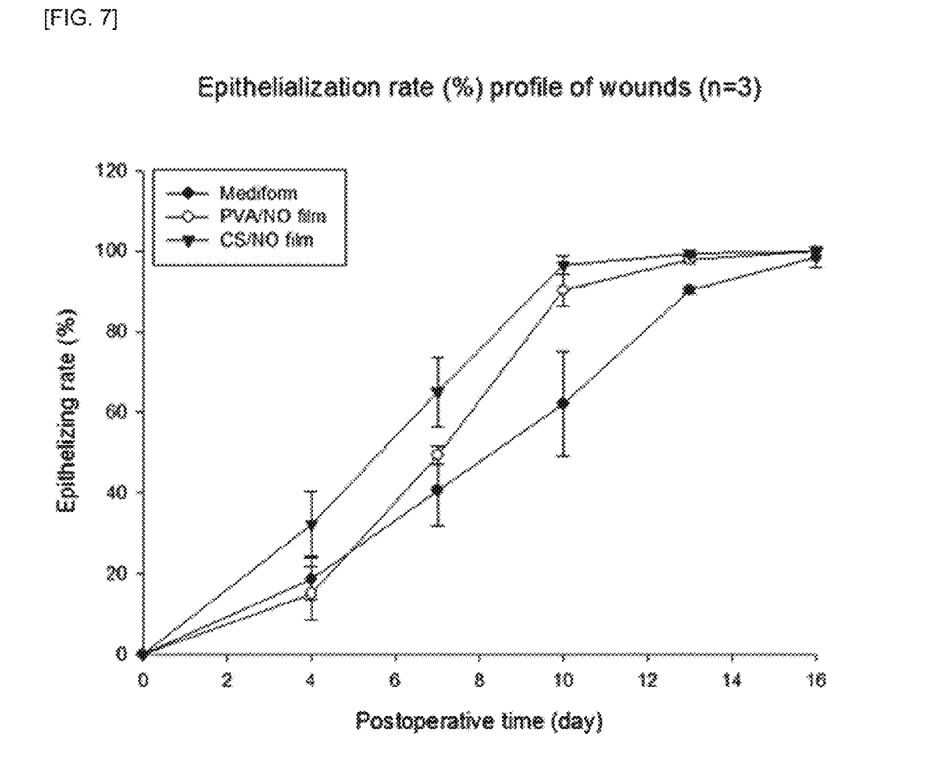
FIG. 7 is epithelialization rate profiles of wounds treated with NO releasing film.

FIG. 7 shows the epithelialization rate profiles of wounds. On POD 4, CS/NO film-treated wounds exhibited higher rates of epithelialization than Mediform-covered wounds. Especially, CS/NO film-treated wounds exhibited highest rates of epithelialization and on POD 7-10, wounds treated with the CS/NO film displayed significantly higher epithelialization rates than those treated with Mediform control.

Accordingly, the NO releasing film has excellent would healing effect and CS/NO film using chitosan as a substrate showed more excellent would healing effect than PVA/NO film using PVA as a substrate. This result indicated that chitosan has the ability to encapsulate and release stably NO, thereby inducing synergy effect of anti-bacteria efficacy of chitosan itself and the wound healing.

8. Histomorphometry

1) Histomorphometry Process

The wound tissue of the skin including the dermis and the subcutaneous tissue collected and one or two regions based on the wound granulation tissue samples, preferably the central region was cut. The cut skin was fixed in 10% neutral buffered formalin. After paraffin-embedding, fragment of 3-4 μm was prepared. Each fragment was stained with hematoxylin and eosin (H&E) for light microscopic investigation, or was stained with Masson's trichrome for collagen fibers. Thereafter, each of the skin was observed by histomorphometry process under an optical microscope (E400, Nikon, Japan).

2) Tissue Morphometry

To identify more detailed histopathological changes, desquamated epithelial regions (mm), number of microvessels in granulation tissues (vessels/$mm^2$ of field), number of infiltrated inflammatory cells in granulation tissues (cells/$mm^2$ of field), percentages of collagen-occupied region in granulation tissues (%/$mm^2$ of field) and granulation tissue areas ($mm^2$/cross trimmed central regions of wounds) were measured on the prepared cross-trimmed individual histological skin samples by using a computer-based automated digital image analyzer (iSolution FL ver 9.1, IMT i-solution Inc., Quebec, Canada). Eight wounds in each group were considered for further analysis in this experiment. In addition, re-epithelializationrates were also calculated as previously known method with modification (Biol Pharm Bull 2007, Dec; 30(12); 2406-2411).

Re-epithelization (%)=[Total length of wound (mm)−desquamated epithelial region (mm)]/Total length of wound (mm)×100

3) Result

Figure 8:
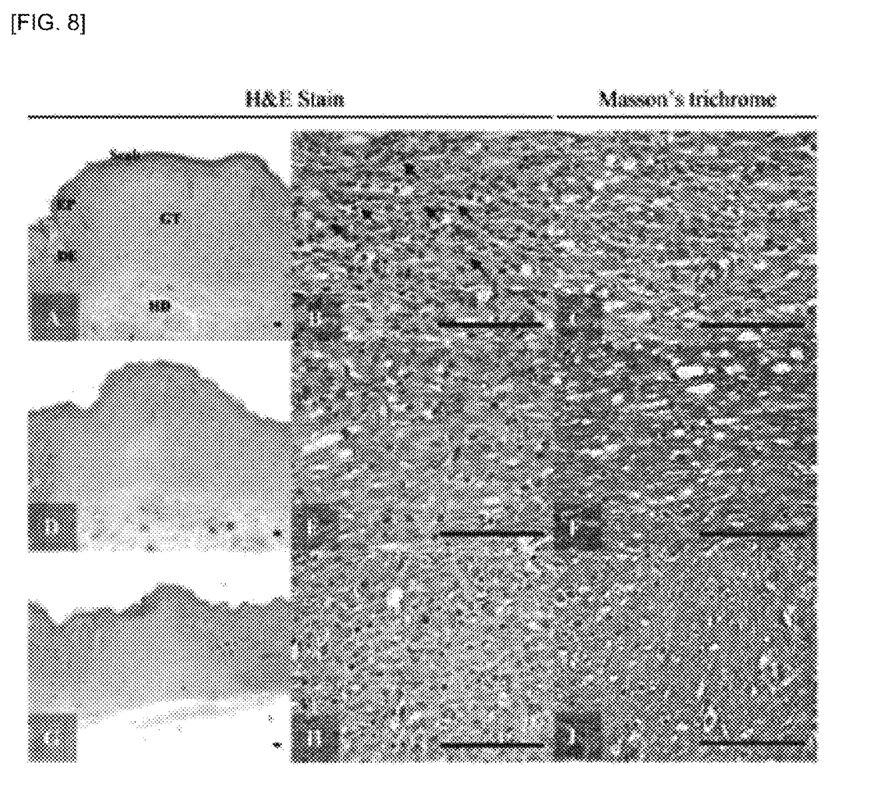
FIG. 8 is representative histopathological profiles of wounds treated with NO releasing film (A-C: gauze control; D-F: NO 0 mg; G-I: NO 10 mg).

FIG. 8 and Table 2 illustrate the histomorphometrical changes in the wounds and histopathological and histomorphometrical comparisons significantly decreases in desquamated epithelial regions and the re-epithelialization rates significantly increased in the film-treated groups compared to those in the control group. Especially, NO releasing film treatment resulted in more favorable and significant accelerating effects on wound healing; more rapid regeneration of wounds, more rapid reconstruction of granulation tissues, lower inflammatory cell infiltration, and lower neovascularization were observed in the NO releasing film-treated group than in the blank film and gauze control group. Furthermore, more favorable rapid collagen fiber regeneration rates were observed in the NO releasing film-treated group.

TABLE 2

| Histomorphometry | Gauze control | Blank film | CS/NO film |
|---|---|---|---|
| Desquamated epithelium regions (mm) | 2.93 ± 0.68 | 1.44 ± 0.22 | 0.61 ± 0.1[ce] |
| Re-epithelization (%) | 70.66 ± 6.79 | 85.58 ± 2.19 | 93.91 ± 0.98[ce] |
| Microvessels numbers | 154.24 ± 28.36 | 66.38 ± 16.15[a] | 30.25 ± 11.72[ab] |
| Infiltrated inflammatory cell numbers | 441.13 ± 122.71 | 139.00 ± 21.53[c] | 79.75 ± 14.27[ce] |
| Collagen occupied regions (%) | 34.32 ± 8.88 | 49.55 ± 7.19[a] | 62.34 ± 6.41[ab] |
| Granulation | 6.39 ± 1.58 | 4.25 ± 0.55[c] | 2.46 ± 0.46[ce] |

TABLE 2-continued

| Histo-morphometry | Gauze control | Blank film | CS/NO film |
|---|---|---|---|
| tissue areas (mm²) | | | |

Values are expressed as mean ± SD of eight rat wounds.
$^a$p < 0.01 as compared with gauze control by the LSD test.
$^b$p < 0.01 as compared with NO of 0 mg by the LSD test.
$^c$p < 0.01 and d p < 0.05 as compared with gauze control by the MW test.
$^e$p < 0.01 as compared with NO of 0 mg by the MW test.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A nitric oxide-releasing wound treatment film comprising S-nitrosoglutathione encapsulated in chitosan.

2. The nitric oxide-releasing wound treatment film of claim 1, comprising the S-nitrosoglutathione of 2.5 to 30 weight %, in respect of the film of 100 weight %.

3. A method of preparing a nitric oxide-releasing wound treatment film, comprising:
   preparing chitosan solution by solubilizing a chitosan in a solvent, adjusting pH and adding glycerol;
   preparing a reaction mixture by adding and mixing S-nitrosoglutathione into the chitosan solution; and
   casting the reaction mixture in form of film and drying it in a dehumidified darkroom.

4. The method of preparing a nitric oxide-releasing wound treatment film of claim 3, wherein the chitosan solution is prepared by adjusting pH 4.0 to pH 6.0 using 0.1M acetic acid buffer solution.

5. The method of preparing a nitric oxide-releasing wound treatment film of claim 3, wherein the S-nitrosoglutathione of 2.5 to 30 parts by weight is added into the chitosan solution of 100 parts by weight.

6. The method of preparing a nitric oxide-releasing wound treatment film of claim 3, wherein the drying is performed at a temperature of 25 to 37° C. for 1 to 2 days.

* * * * *